United States Patent
Lee et al.

(10) Patent No.: US 11,896,706 B2
(45) Date of Patent: Feb. 13, 2024

(54) COMPOSITION FOR PREVENTING HAIR LOSS OR PROMOTING HAIR GROWTH, COMPRISING, AS ACTIVE INGREDIENT, MIXED EXTRACT OF CUCUMBER, EGGPLANT AND SNAIL EXTRACTS AS ACTIVE INGREDIENT

(71) Applicant: OGADAL INC., Gyeonggi-do (KR)

(72) Inventors: Dong wan Lee, Seoul (KR); Seoung Ok Kim, Gyeonggi-do (KR); Haseop Lee, Gyeonggi-do (KR)

(73) Assignee: OGADAL INC., Gyeonggi-do (KR)

( * ) Notice: Subject to any disclaimer, the term of this patent is extended or adjusted under 35 U.S.C. 154(b) by 0 days.

(21) Appl. No.: 17/295,745

(22) PCT Filed: Jun. 23, 2020

(86) PCT No.: PCT/KR2020/008183
§ 371 (c)(1),
(2) Date: Jul. 28, 2021

(87) PCT Pub. No.: WO2021/149880
PCT Pub. Date: Jul. 29, 2021

(65) Prior Publication Data
US 2022/0347081 A1 Nov. 3, 2022

(30) Foreign Application Priority Data
Jan. 22, 2020 (KR) ........................ 10-2020-0008815

(51) Int. Cl.
| | | |
|---|---|---|
| *A61K 8/9783* | (2017.01) | |
| *A61K 8/9767* | (2017.01) | |
| *A61K 8/98* | (2006.01) | |
| *A61Q 5/00* | (2006.01) | |
| *A61Q 7/00* | (2006.01) | |
| *A61K 36/42* | (2006.01) | |
| *A61K 35/618* | (2015.01) | |
| *A61K 8/9761* | (2017.01) | |
| *A61P 17/14* | (2006.01) | |
| *A61K 36/489* | (2006.01) | |
| *A61K 36/14* | (2006.01) | |
| *A61K 36/81* | (2006.01) | |
| *A61K 36/9068* | (2006.01) | |

(52) U.S. Cl.
CPC .......... *A61K 8/9783* (2017.08); *A61K 8/9761* (2017.08); *A61K 8/9767* (2017.08); *A61K 8/98* (2013.01); *A61K 35/618* (2013.01); *A61K 36/42* (2013.01); *A61K 36/489* (2013.01); *A61K 36/81* (2013.01); *A61K 36/9068* (2013.01); *A61P 17/14* (2018.01); *A61Q 5/002* (2013.01); *A61Q 7/00* (2013.01); *A61K 36/14* (2013.01)

(58) Field of Classification Search
None
See application file for complete search history.

(56) References Cited

FOREIGN PATENT DOCUMENTS

| GB | 2146528 A | * | 4/1985 | ............... A61K 8/66 |
|---|---|---|---|---|
| KR | 1020030017172 | * | 3/2003 | |
| KR | 1020070079596 | | 8/2007 | |
| KR | 1020170100832 | | 9/2017 | |
| KR | 1020180006014 | * | 1/2018 | |
| KR | 1020180021283 | | 3/2018 | |

OTHER PUBLICATIONS

Machine translation of KR1020180006014.*
Mukherjee (Mukherjee, P.J., et al., Phytochemical and therapeutic potential of cucumber, Fitoterapia, vol. 84, Jan. 2013, pp. 227-236) (Year: 2013).*

* cited by examiner

*Primary Examiner* — H. Sarah Park
(74) *Attorney, Agent, or Firm* — DUANE MORRIS LLP; Gregory M. Lefkowitz; Brandon A. Chan (57) ABSTRACT

The present disclosure relates to a composition for preventing hair loss or promoting hair growth, which contains a mixture of cucumber, eggplant and snail extracts as an active ingredient. The composition according to the present disclosure, which contains a mixture of cucumber, eggplant and snail extracts as an active ingredient, has been confirmed to increase the expression of hepatocyte growth factor (HGF), keratinocyte growth factor (KGF) and insulin-like growth factor 1 (IGF-1) in dermal papilla cells which are known to play a critical role in the induction of new hair follicles and maintenance of hair growth, exhibit hair-growing effect comparable to that of minoxidil in a hair growth test for depilated 6-week-old C57BL/6 mice, and exhibit hair loss-improving effect in a clinical test for human. Accordingly, it can be usefully used as a cosmetic composition or a pharmaceutical composition for external application to skin for preventing hair loss or promoting hair growth.

7 Claims, 2 Drawing Sheets

COMPOSITION FOR PREVENTING HAIR LOSS OR PROMOTING HAIR GROWTH, COMPRISING, AS ACTIVE INGREDIENT, MIXED EXTRACT OF CUCUMBER, EGGPLANT AND SNAIL EXTRACTS AS ACTIVE INGREDIENT

CROSS-REFERENCE TO RELATED APPLICATIONS

This application is a § 371 national stage entry of International Application No. PCT/KR2020/008183, filed on Jun. 23, 2020, which claims priority to Korean Patent Application No. 10-2020-0008815, filed on Jan. 22, 2021, the entire contents of which are incorporated herein by reference.

TECHNICAL FIELD

The present disclosure relates to a composition for preventing hair loss or promoting hair growth, which contains a mixture of cucumber, eggplant and snail extracts as an active ingredient, particularly to a cosmetic composition and a pharmaceutical composition for external application to skin.

BACKGROUND ART

Hair is one of skin appendages. It is morphologically derived from the epithelium and is formed from 2 months after birth. Hair is classified into thin vellus hair, and thick and hard terminal hair depending on its thickness. Hair grows with a specific cycle and does not shed at once. Each hair follicle passes through active and resting stages. During the growing phase, i.e., anagen, cells in the hair bulb grow actively, leading to hair growth. In human hair, 85% of the hair follicles are in the growing phase lasting 3-6 years, 5% in the catagen lasting 2-3 weeks where the hair follicles begin to shrink, and the remaining 10% in the telogen lasting 3-4 months where hair growth stops, and about 50-100 hairs are shed daily on average (Jin-san Lee (1998). Hair Graying and Hair Loss, Dongui Bogam, Healthy Lifestyle Research Group, Inhwa Publishing). The causes of hair loss include genetic factors, malnutrition, endocrine disorders, tissue disorders, demodex, compression on the head, dandruff, autoimmune disorder, topical infection, etc. (Min-jeong Kim (2005). Hair and Scalp, Yelim, pp. 110-111). It is though that hair loss is caused by the disorder of metabolism of hormones, proteins, etc. in hair follicles, which are closely related with hair growth, and the change in many social and cultural factors that may affect hair loss directly or indirectly, such as increased stress due to increased social activities in modern society, nutritional imbalance owing to westernized eating habits, etc. (*J. Kor. Soc. Cosm.* Vol. 13, No. 3 (2007), pp. 1366-1375.).

Hair loss can be largely classified into two types. The first type, which is called male-pattern baldness, alopecia senilis or androgenic alopecia, is frequently found in middle-aged men and hair loss begins at the frontal and parietal. The second type, which is called alopecia areata, begins mainly at the occipital and shows round or oval bald patches with relatively distinct boundaries. This hair loss can occur even in adolescence. Hair loss is not limited to men but may occur also in women. Particularly for women, hair loss often begins at the parietal and alopecia areata also occurs, although the frequency is lower than in men (M. Inaba et al., Androgenetic Alopecia, Springer-Berlag, Tokyo, Japan, 1996).

Medical and traditional approaches are currently available for prevention and treatment of hair loss. The medical approaches include medication, surgery, nutrition therapy, dietary supplements, etc. At present, minoxidil (MXD) and finasteride are approved by the Food and Drug Administration (FDA) as medications that promote hair growth. But, hair loss occurs again if medication is stopped and it is reported that long-term use results in side effects such as dermatitis, etc. (Kaufman K. D. (1996), *Elsevier Science,* pp. 363-365).

REFERENCES OF RELATED ART

Non-Patent Documents

Jin-san Lee (1998). Hair Graying and Hair Loss, Dongui Bogam, Healthy Lifestyle Research Group, Inhwa Publishing.

Min-jeong Kim (2005). Hair and Scalp, Yelim, pp. 110-111.

*J. Kor. Soc. Cosm.* Vol. 13, No. 3 (2007), pp. 1366-1375.

M. Inaba et al., Androgenetic Alopecia, Springer-Berlag, Tokyo, Japan, 1996.

Kaufman K. D. (1996) Elsevier Science, pp. 363-365.

DISCLOSURE

Technical Problem

The present disclosure is directed to providing a composition for preventing hair loss or promoting hair growth, containing a mixture of cucumber, eggplant and snail extracts as an active ingredient, which increases the expression of hepatocyte growth factor (HGF), keratinocyte growth factor (KGF) and insulin-like growth factor 1 (IGF-1) in dermal papilla cells, exhibits hair-growing effect comparable to that of minoxidil in a hair growth test for depilated 6-week-old C57BL/6 mice, and exhibits hair loss-improving effect in a clinical test for human.

Technical Solution

The present disclosure provides a composition for preventing hair loss or promoting hair growth, which contains a mixture of cucumber, eggplant and snail extracts as an active ingredient.

The composition may further contain a mixture of thuja leaf and sophora root extracts.

The composition may further contain an extract of one or more of dried dihuang, dried ginger rhizome, Chinese angelica root, eclipta, *Cynanchum wilfordii,* foxtail millet and brown rice.

The composition may further contain an extract of one or more selected from houttuynia and licorice.

The composition may be a cosmetic composition.

The cosmetic composition may be formulated as one of a hair tonic, a hair conditioner, a hair essence, a hair lotion, a hair-nourishing lotion, a hair shampoo, a hair rinse, a hair treatment, a hair cream, a hair-nourishing cream, a hair-moisturizing cream, a hair massage cream, a hair wax, a hair aerosol, a hair pack, a hair-nourishing pack, a hair soap, a hair-cleansing foam, a hair oil, a hair-drying preparation, a hair-preserving preparation, a hair dye, a hair-waving preparation, a hair bleach, a hair gel, a hair glaze, a hairdressing preparation, a hair lacquer, a hair moisturizer, a hair mousse and a hair spray.

The composition may be a pharmaceutical composition for external application to skin.

The pharmaceutical composition for external application to skin may be any pharmaceutical composition for external application to skin selected from a cream, a gel, a patch, a spray, an ointment, a plaster, a lotion, a liniment, a paste and a cataplasm.

Advantageous Effects

A composition for preventing hair loss or promoting hair growth of the present disclosure, which contains a mixture of cucumber, eggplant and snail extracts as an active ingredient, is a natural substance which does not exhibit cytotoxicity for human fibroblasts and dermal papilla cells. It has been confirmed to increase the expression of hepatocyte growth factor (HGF), keratinocyte growth factor (KGF) and insulin-like growth factor 1 (IGF-1) in dermal papilla cells which are known to play a critical role in the induction of new hair follicles and maintenance of hair growth, exhibit hair-growing effect comparable to that of minoxidil in a hair growth test for depilated 6-week-old C57BL/6 mice, and exhibit hair loss-improving effect in a clinical test for human.

BEST MODE

The present disclosure relates to a composition for preventing hair loss or promoting hair growth, which contains a mixture of cucumber, eggplant and snail extracts as an active ingredient, particularly to a cosmetic composition, a pharmaceutical composition for external application to skin or a functional health food composition.

Hereinafter, the present disclosure is described in more detail.

Cucumber is an annual creeping vine plant in the family Cucurbitaceae. It has been developed into various cultivars and is cultivated globally as a vegetable. Its fruit is edible. Cucumber contains 95% or more of water and small amounts of various vitamins and minerals and is rich in ascorbinase.

Specifically, the cucumber used in the composition is the fruit with the bitter-tasting top and bottom ends of about 1-3 cm removed. More specifically, the seeds of cucumber may be removed to enhance the activity of preventing hair loss and promoting hair growth.

Eggplant is annual in temperate areas but perennial in the tropics. It is native to India and is cultivated throughout in tropical and temperate climates. The fruit is eaten after being steamed or fried. In Korea, it has been cultivated from the Shilla Dynasty. It was introduced to Europe in the 13th century, but has not been cultivated actively as food as in East Asia.

Specifically, the eggplant used in the composition is one with the stalk removed for enhancing the activity of preventing hair loss and promoting hair growth.

Snail collectively refers to the mollusks belonging to the class Gastropoda. In Korea, about 35 species are known, including navel snail, left-handed snail, true snail, bride snail, etc. According to Dongui Bogam, snail has cold nature and salty taste, is slightly toxic, treats anal prolapse, and relieves thirst.

Specifically, the snail used in the composition is one with the internal organs removed. More specifically, after steaming snail for 5-30 minutes, the internal organs may be removed for enhancing the activity of preventing hair loss and promoting hair growth.

In the present disclosure, the composition or the mixture of the extracts includes not only an extract obtained by mixing the respective materials and then extracting the same using an extraction solvent but also an extract obtained by extracting the respective materials and then mixing the same.

The composition may contain a mixture of cucumber or a cucumber extract at a solid content of 4-16 parts by weight, specifically 8-16 parts by weight, eggplant or an eggplant extract at a solid content of 2-8 parts by weight, specifically 4-8 parts by weight, and snail or a snail extract at a solid content of 1-4 parts by weight. When one or more of the ingredients of the composition is missing or its content is outside the above-described range, the expression of at least one gene of insulin-like growth factor 1 (IGF-1), hepatocyte growth factor (HGF) and keratinocyte growth factor (KGF), which are associated with the activity of preventing hair loss and promoting hair growth, is decreased.

In the present disclosure, the composition or the extract may be extracted with water, an organic solvent or a combination thereof. The organic solvent may be a $C_1$-$C_4$ alcohol, acetone, chloroform, methylene chloride, ether, ethyl acetate, hexane or a combination thereof, although not being limited thereto. The $C_1$-$C_4$ alcohol may be, for example, methanol, ethanol, propanol or butanol. Ethanol is preferred the most. The extraction solvent may be used in an amount of 2-20 times, specifically 4-10 times, the weight of the raw material.

The extract may be prepared by any extraction method known to those skilled in the art in the field of natural substance extraction. For example, it may be prepared by conducting hot water extraction, cold precipitation extraction, reflux condensation extraction or ultrasonic extraction at an extraction temperature of 20-100° C., specifically about 50-90° C., for 1-30 hours, specifically by conducting hot water extraction continuously for 1-5 times. After filtering the obtained extract under reduced pressure and removing the solvent from using a vacuum evaporator, an extract may be obtained by freeze-drying the same.

The composition may further contain a mixture of thuja leaf and sophora root extracts.

Thuja leaf refers to the young branch and leaf of thuja (*Thuja orientalis* L.) which belongs to the family Cupressaceae. Thuja leaf is used for treating nosebleed, hematemesis, bloody excrement, hematuria and metrorrhagia because it relieves blood heat, and is also used for cough, asthma, phlegm, hair loss, seborrheic dermatitis, traumatic bleeding, etc. It has been reported to be pharmacologically effective for reducing bleeding time, relieving cough and phlegm, lowering blood pressure, relieving asthma, etc. in addition to antibacterial activity. Scale-like small leaves are arranged in alternating pairs, and the middle lobe is rhombic.

Sophora root refers to the root of *Sophora flavescens*, a perennial herb in the family Fabaceae. It is known to contain alkaloids such as matrine, oxymatrine, sophoranol, anazirine, methylcysteine, baptifolin, etc. and flavonoids such as xanthohumol, isoxanthohumol, etc., and is known to have diuretic, antiarrhythmic and antibacterial activities.

Specifically, the composition may contain thuja leaf or a thuja leaf extract at a solid content of 2-8 parts by weight and sophora root or a sophora root extract at a solid content of 2-8 parts by weight for enhancing the effect of preventing hair loss and promoting hair growth.

The composition may further contain an extract of one or more selected from dried dihuang, dried ginger rhizome, Chinese angelica root, eclipta and *Cynanchum wilfordii*, foxtail millet and brown rice.

The composition may further contain dried dihuang or a dried dihuang extract at a solid content of 1-4 parts by weight, dried ginger rhizome or a dried ginger rhizome extract at a solid content of 1-4 parts by weight, Chinese angelica root or a Chinese angelica root extract at a solid content of 1-4 parts by weight, eclipta or an eclipta extract at a solid content of 1-4 parts by weight, *Cynanchum wilfordii* or an *Cynanchum wilfordii* extract at a solid content of 1-4 parts by weight, foxtail millet or a foxtail millet extract at a solid content of 1-4 parts by weight, or brown rice or a brown rice extract at a solid content of 1-4 parts by weight for lowering cytotoxicity for human fibroblasts and dermal papilla cells while maintaining the activity of preventing hair loss and promoting hair growth.

In addition, the composition may further contain an extract of one or more selected from houttuynia and licorice.

The composition may further contain houttuynia or a houttuynia extract at a solid content of 1-4 parts by weight, or licorice or a licorice extract at a solid content of 1-4 parts by weight for improving scalp inflammation, scalp itching and dandruff while maintaining the activity of preventing hair loss and promoting hair growth.

The mixture of cucumber, eggplant and snail extracts, the mixture of cucumber, eggplant, snail, thuja leaf and sophora root extracts, or the extracts other natural substances contained in the composition are natural substances commonly used as natural medicines. They may be contained in the composition of specifically 0.001-90 wt %, more specifically 0.001-10 wt %, based on the total weight of the composition, although not being particularly limited thereto.

The composition of the present disclosure may be used as a cosmetic composition or a pharmaceutical composition for external application to skin for the effect of preventing hair loss and promoting hair growth.

When the composition of the present disclosure is used as a cosmetic composition, it may further contain, in addition to the mixture of cucumber, eggplant and snail extracts an active ingredient, ingredients commonly used in a cosmetic composition, e.g., a water-soluble vitamin, an oil-soluble vitamin, a polypeptide, a polysaccharide, a sphingolipid, a seaweed extract, etc.

The water-soluble vitamin may be any one that can be used in cosmetic products. Specifically, the water-soluble vitamin that may be used in the present disclosure may include vitamin $B_1$, vitamin $B_2$, vitamin $B_6$, pyridoxine, pyridoxine chloride, vitamin $B_{12}$, pantothenic acid, nicotinic acid, nicotinamide, folic acid, vitamin C, vitamin H, etc., salts thereof (thiamine hydrochloride, sodium ascorbate, etc.) or derivatives thereof (ascorbic acid-2-sodium phosphate, ascorbic acid-2-magnesium phosphate, etc.). The water-soluble vitamin may be obtained by common methods such as microbial conversion, purification from microbial culture, enzymatic method, chemical synthesis, etc.

The oil-soluble vitamin may be any one that can be used in cosmetic products. Specifically, the water-soluble vitamin that may be used in the present disclosure may include vitamin A, carotene, vitamin $D_2$, vitamin $D_3$, vitamin E (D-alpha-tocopherol or L-alpha-tocopherol), etc., derivatives thereof (ascorbyl palmitate, ascorbyl stearate, ascorbyl dipalmitate, D/L-alpha-tocopherol acetate, D/L-alpha-tocopherol vitamin E nicotinate, D/L-pantothenyl alcohol, D-pantothenyl alcohol, pantothenyl ethyl ether, etc.), etc. The oil-soluble vitamin may be obtained by common methods such as microbial conversion, purification from microbial culture, enzymatic method, chemical synthesis, etc.

The polypeptide may be any one that can be used in cosmetic products. Specifically, collagen, hydrolyzed collagen, gelatin, elastin, hydrolyzed elastin, keratin, etc. may be used. The polypeptide may be purified and obtained by common methods such as purification from microbial culture, enzymatic method, chemical synthesis, etc., or may be purified from natural substances such as the epidermis of pig, cow, etc., the silk of silkworm, etc.

The polysaccharide may be any one that can be used in cosmetic products. Specifically, hydroxyethyl cellulose, xanthan gum, sodium hyaluronate, chondroitin sulfate or its salt (e.g., sodium salt), etc. may be used. For example, chondroitin sulfate or its salt may be generally purified from mammals or fish.

The sphingolipid may be any one that can be used in cosmetic products. Specifically, ceramides, phytosphingosine, sphingoglycolipids, etc. may be used. The sphingolipids may be generally purified from mammals, fish, shellfish, yeast, plants, etc. or may be obtained by chemical synthesis.

The seaweed extract may be any one that can be used in cosmetic products. Specifically, a brown algae extract, a red algae extract, a green algae extract, etc., or carrageenan, alginic acid, sodium alginate, potassium alginate, etc. purified from the seaweed extract may be used. The seaweed extract may be purified and obtained from seaweed by common methods.

If necessary, the cosmetic composition may contain other ingredients commonly used in cosmetic products in addition to the ingredient described above.

The ingredients that may be further added may include an oil or fat, a humectant, an emollient, a surfactant, an organic or inorganic pigment, an organic powder, a UV absorbent, an antiseptic, a sterilizer, an antioxidant, a plant extract, a pH control agent, an alcohol, a colorant, a flavor, a blood circulation accelerator, a cooling agent, an antiperspirant, purified water, etc.

The oil or fat may include an ester-based oil or fat, a hydrocarbon-based oil or fat, a silicon-based oil or fat, a fluorine-based oil or fat, an animal oil or fat, a plant oil or fat, etc.

The ester-based oil or fat may be glyceryl tri-2-ethylhexanoate, cetyl 2-ethylhexanoate, isopropyl myristate, butyl myristate, isopropyl palmitate, ethyl stearate, octyl palmitate, isocetyl isostearate, butyl stearate, ethyl linoleate, isopropyl linoleate, ethyl oleate, isocetyl myristate, isostearyl myristate, isostearyl palmitate, octyldodecyl myristate, diethyl sebacate, diisopropyl adipate, isoalkyl neopentanoate, glyceryl tri(capryl caprate), trimethylolpropane tri-2-ethylhexanoate, trimethylolpropane triisostearate, pentaerythritol tetra-2-ethylhexanoate, cetyl caprylate, decyl laurate, hexyl laurate, decyl myristate, myristoyl myristate, cetyl myristate, stearyl stearate, decyl oleate, cetyl ricinoleate, isostearyl laurate, isotridecyl myristate, isocetyl palmitate, octyl stearate, isocetyl stearate, isodecyl oleate, octyldodecyl oleate, octyldodecyl linoleate, isopropyl isostearate, cetostearyl 2-ethyl hexanoate, stearyl 2-ethylhexanoate, hexyl isostearate, ethylene glycol dioctanoate, ethylene glycol dioleate, propylene glycol dicaprate, propylene glycol di(capryl caprate), propylene glycol dicaprylate, neopentyl glycol dicaprate, neopentyl glycol dioctanoate, glyceryl tricaprylate, glyceryl triundecylate, glyceryl triisopalmitate, glyceryl triisostearate, octyldodecyl neopentanoate, isostearyl octanoate, octyl isonononanoate, hexyldecyl neodecanoate, octyldodecyl neodecanoate, isostearyl isostearate, octyldecyl isostearate, polyglyceryl oleate, polyglyceryl isostearate, triisocetyl citrate, triisoalkyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, di-2-ethylhexyl succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyl hydroxystearate, stearyl 12-stearoyl hydroxystearate, isostearyl 12-stearoyl hydroxystearate, etc.

The hydrocarbon-based oil or fat may be squalane, liquid paraffin, an a-paraffin, isoparaffin, ceresin, paraffin, liquid isoparaffin, polybutene, microcrystalline wax, vaseline, etc.

The silicon-based oil or fat may be polymethylsilicone, methylphenylsilicone, methylcyclopolysiloxane, octamethylpolysiloxane, decamethylpolysiloxane, dodecamethylcyclosiloxane, a dimethylsiloxane-methylcetyloxysiloxane copolymer, a dimethylsiloxane-methylstearoyloxysiloxane copolymer, alkyl-modified silicone oil, amino-modified silicone oil, etc.

The fluorine-based oil or fat may be perfluoropolyether, etc.

The animal or plant oil or fat may be avocado oil, almond oil, olive oil, sesame oil, rice bran oil, safflower oil, soybean oil, corn oil, rapeseed oil, apricot oil, palm kernel oil, palm oil, castor oil, sunflower oil, grape seed oil, cotton seed oil, coconut oil, kukui nut oil, wheat germ oil, rice germ oil, shea butter, evening primrose oil, macadamia nut oil, meadowfoam oil, yolk oil, beef tallow, horse oil, mink oil, orange roughy oil, jojoba oil, candelilla wax, carnauba wax, liquid lanolin, hydrogenated castor oil, etc.

The humectant may be a water-soluble low-molecular-weight humectant, an oil-soluble low-molecular-weight humectant, a water-soluble polymer, an oil-soluble polymer, etc.

The water-soluble low-molecular-weight humectant may be serine, glutamine, sorbitol, mannitol, sodium pyrrolidone carboxylate, glycerin, propylene glycol, 1,3-butylene glycol, ethylene glycol, polyethylene glycol B (degree of polymerization n=2 or higher), polypropylene glycol (degree of polymerization n=2 or higher), polyglycerin B (degree of polymerization n=2 or higher), lactic acid, lactate, etc.

The oil-soluble low-molecular-weight humectant may be cholesterol, cholesteryl ester, etc.

The water-soluble polymer may be carboxyvinyl polymer, polyaspartate, tragacanth, xanthan gum, methyl cellulose, hydroxymethyl cellulose, hydroxyethyl cellulose, hydroxypropyl cellulose, carboxymethyl cellulose, water-soluble chitin, chitosan, dextrin, etc.

The oil-soluble polymer may be a polyvinylpyrrolidone-eicosene copolymer, a polyvinylpyrrolidone-hexadecene copolymer, nitrocellulose, a dextrin fatty acid ester, high-molecular-weight silicone, etc.

The emollient may be long-chain acyl glutamic acid cholesteryl ester, cholesteryl hydroxystearate, 12-hydroxystearic acid, stearic acid, rosin acid, lanolin fatty acid cholesteryl ester, etc.

The surfactant may be may be a nonionic surfactant, an anionic surfactant, a cationic surfactant, an amphoteric surfactant, etc.

The nonionic surfactant may be self-emulsifying glyceryl monostearate, propylene glycol fatty acid ester, glycerin fatty acid ester, polyglycerin fatty acid ester, sorbitan fatty acid ester, polyoxyethylene (POE) sorbitan fatty acid ester, POE sorbitol fatty acid ester, POE glycerin fatty acid ester, POE alkyl ether, POE fatty acid ester, POE hydrogenated castor oil, POE castor oil, polyoxyethylene/polyoxypropylene (POE/POP) copolymer, POE/POP alkyl ether, polyether-modified silicone, lauric alkanolamide, alkylamine oxide, hydrogenated soybean phospholipid, etc.

The anionic surfactant may be fatty acid soap, α-acyl sulfonate, alkyl sulfonate, alkylaryl sulfonate, alkyl naphthalenesulfonate, alkyl sulfate, POE alkyl ether sulfate, alkyl amide sulfate, alkyl phosphate, POE alkyl phosphate, alkyl amide phosphate, alkyloyl alkyl taurate, N-acylamino acid salt, POE alkyl ether carboxylate, alkyl sulfosuccinate, sodium alkyl sulfoacetate, acylated hydrogenated collagen peptide, perfluoroalkyl phosphate ester, etc.

The cationic surfactant may be alkyl trimethylammonium chloride, stearyl trimethylammonium chloride, stearyl trimethylammonium bromide, cetostearyl trimethylammonium chloride, distearoyl dimethylammonium chloride, stearyl dimethylbenzylammonium chloride, behenyl trimethylammonium bromide, benzalkonium chloride, diethylaminoethylamide stearate, dimethylaminopropylamide stearate, a quaternary ammonium salt of a lanolin derivative, etc.

The amphoteric surfactant may be carboxybetaine, amidobetaine, sulfobetaine, hydroxysulfobetaine, am idosulfobetaine, phosphobetaine, am inocarboxylate, an imidazoline derivative, amidoamine, etc.

The organic or inorganic pigment may be an inorganic pigment such as silicic acid, silica, magnesium silicate, talc, sericite, mica, kaolin, rouge, clay, bentonite, titanium-coated mica, bismuth oxychloride, zirconium oxide, magnesium oxide, zinc oxide, titanium oxide, aluminum oxide, calcium sulfate, barium sulfate, magnesium sulfate, calcium carbonate, magnesium carbonate, iron oxide, ultramarine, chromium oxide, chromium hydroxide, calamine and complexes thereof, an organic pigment such as polyamide, polyester, polypropylene, polystyrene, polyurethane, vinyl resin, urea resin, phenol resin, fluorine resin, silicon resin, acrylic resin, melamine resin, epoxy resin, polycarbonate resin, a divinylbenzene-styrene copolymer, silk powder, cellulose, CI pigment yellow, CI pigment orange, etc., or a mixture of an inorganic pigment and an organic pigment.

The organic powder may be metallic soap such as calcium stearate, an alkyl metal phosphate such as zinc sodium cetylate, zinc laurate, calcium laurate, etc., a polyvalent metal salt of an acylamino acid such as N-lauroyl-β-alaninecalcium, N-lauroyl-β-alaninezinc, N-lauroylglycinecalcium, etc., an amidosulfonic acid polyvalent metal salt such as N-lauroyltaurinecalcium, N-palmitoyltaurinecalcium, etc., a N-actyl basic amino acid such as N-ε-lauroyl-L-lysine, N-ε-palmitoyllysine, N-α-palmitoylornithine, N-α-lauroylarginine, N-α-hydrogenated tallow fatty acid acylarginine, etc., a N-acylpolypeptide such as N-lauroylglycylgylcine, etc., an α-amino fatty acid such as α-aminocaprylic acid, α-aminolauric acid, etc., polyethylene, polypropylene, nylon, polymethyl mathacrylate, polystyrene, a divinylbenzene-styrene copolymer, tetrafluoroethylene, etc.

The UV absorbent may be p-aminobezoic acid, ethyl p-aminobenzoate, amyl p-aminobenzoate, octyl p-aminobenzoate, ethylene glycol salicylate, phenyl salicylate, octyl salicylate, benzyl salicylate, butylphenyl salicylate, homomenthyl salicylate, benzyl cinnamate, 2-ethoxyethyl p-methoxycinnamage, octyl p-methoxycinnamage, mono-2- ethylhexaneglyceryl di-p-methoxycinnamage, isopropyl p-methoxycinnamage, a mixture of diisopropyl and diisopropyl cinnamic acid esters, urocanic acid, ethyl urocanate, hydroxymethoxyenzophenone, hydroxymethoxyenzophenonesulfonic acid and its salts, dihydroxymethoxyenzophenone, sodium dihydroxymethoxyenzophenonedisulfonate, dihydroxyenzophenone, tetrahydroxyenzophenone, 4-tert-butyl-4'-methoxydibenzoylmethane, 2,4,6-trianilino-p-(carbo-2'-ethylhexyl-1'-oxy)-1,3,5-triazine, 2-(2-hydroxy-5-methylphenyl)benzotriazole, etc.

The sterilizer may be hinokitiol, triclosan, trichlorohydroxydiphenyl ether, chlorhexidine gluconate, phenoxyethanol, resorcin, isopropylmethylphenol, azulene, salicylic acid, zinc pyrithione, benzalkonium chloride, photosensitizer 301, mononitroguaiacol sodium, undecylenic acid, etc.

The antioxidant may be butylhydroxyanisole, propyl gallate, erythorbic acid, etc.

The pH control agent may be citric acid, sodium citrate, malic acid, sodium malate, fumaric acid, sodium fumarate, succinic acid, sodium succinate, sodium hydroxide, sodium monohydrogen phosphate, etc.

The alcohol may be a higher alcohol such as cetyl alcohol, etc.

The additionally added ingredients are not limited to those described above, and any of the above-described ingredients may be used within a range not negatively affecting the purpose and effect of the present disclosure, specifically in an amount of 0.001-50 wt %, more specifically 0.001-3 wt %, based on the total weight of the composition.

The cosmetic composition of the present disclosure may be in the form of a solution, an emulsion, a viscous mixture, etc.

The ingredients contained in the cosmetic composition of the present disclosure may include, in addition to the active ingredient, an ingredient commonly used in a cosmetic composition, e.g., a common adjuvant or carrier such as a stabilizer, a solubilizer, a vitamin, a pigment and a flavor.

The cosmetic composition of the present disclosure may be prepared into any formulation commonly prepared in the art, e.g., a paste, a cream, a gel, a powder, a spray, a solution, an emulsion, a suspension, a lotion, a soap, a treatment, a surfactant-containing cleanser, an oil, a powder foundation, an emulsion foundation, a wax foundation, etc., although not being limited thereto.

More specifically, it may be prepared into a formulation such as a skin lotion, a skin softener, a skin toner, an astringent, a lotion, a milk lotion, a moisturizing lotion, nourishing lotion, a massage cream, a nourishing cream, a moisturizing cream, a hand cream, a foundation, an essence, a nourishing essence, a pack, a soap, a cleansing foam, a cleansing lotion, a cleansing cream, a body lotion or a body cleanser.

When the formulation of the present disclosure is a paste, a cream or a gel, an animal fiber, a plant fiber, a wax, paraffin, starch, tragacanth, a cellulose derivative, polyethylene glycol, silicon, bentonite, silica, talc, zinc oxide, etc. may be used as a carrier ingredient.

When the formulation of the present disclosure is a powder or a spray, lactose, talc, silica, aluminum hydroxide, calcium silicate or polyamide powder may be used as a carrier ingredient. Particularly, a spray may further contain a propellant such as chlorofluorohydrocarbon, propane/butane or dimethyl ether.

When the formulation of the present disclosure is a solution or an emulsion, a solvent, a solubilizer or an emulsifier may be used as a carrier ingredient. Examples include water, ethanol, isopropanol, ethyl carbonate, ethyl acetate, benzyl alcohol, benzyl benzoate, propylene glycol, 1,3-butylglycol oil, glycerol aliphatic ester, polyethylene glycol or fatty acid ester of sorbitan.

When the formulation of the present disclosure is a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier ingredient.

When the formulation of the present disclosure is a surfactant-containing cleanser, aliphatic alcohol sulfate, aliphatic alcohol ether sulfate, sulfosuccinic acid monoester, isethionate, an imidazolinium derivative, methyl taurate, sarcosinate, fatty acid amide ether sulfate, alkyl amidobetaine, aliphatic alcohol, fatty acid glyceride, fatty acid diethanolamide, vegetable oil, a lanolin derivative, ethoxylated glycerol fatty acid ester, etc. may be used as a carrier ingredient When the composition of the present disclosure is used as a pharmaceutical composition for external application to skin, it may contain 0.1-50 wt % of a mixture of cucumber, eggplant and snail extracts as an active ingredient, based on the total weight of the composition.

The pharmaceutical composition for external application to skin of the present disclosure may further contain an adequate carrier, excipient or diluent commonly used for preparation of a pharmaceutical composition.

The pharmaceutical composition of the present disclosure may be formulated into an oral formulation such as a powder, a granule, a tablet, a capsule, a suspension, an emulsion, a syrup, an aerosol, etc., a formulation for external application, a suppository and a sterilized injection solution according to common methods. The carrier, excipient or diluent that may be contained in the pharmaceutical composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate and mineral oil. The formulation is prepared using a commonly used diluent or excipient such as a filler, an extender, a binder, a wetting agent, a disintegrant, a surfactant, etc. Solid formulations for oral administration include a tablet, a pill, a powder, a granule, a capsule, etc. and these solid formulations are prepared by mixing the active ingredient with at least one excipient, e.g., starch, calcium carbonate, sucrose, lactose, gelatin, etc. In addition, a lubricant such as magnesium stearate or talc is used in addition to the simple excipient. Liquid formulations for oral administration include a suspension, a liquid formulation for internal use, an emulsion, a syrup, etc. and may contain various excipients, e.g., a wetting agent, a sweetener, an aromatic, a preservative, etc. in addition to the commonly used simple diluent such as water and liquid paraffin. Formulations for parenteral administration include a sterilized aqueous solution, a nonaqueous solution, a suspension, an emulsion, a lyophilized preparation and a suppository. As the nonaqueous solution or suspension, propylene glycol, polyethylene glycol, vegetable oil such as olive oil, an injectable ester such as ethyl oleate, etc. may be used. As a base of the suppository, witepsol, macrogol, Tween 61, cocoa butter, laurin butter, glycerogelatin, etc. may be used. Specifically, a pharmaceutical composition in the form of a formulation for external application to skin, such as an ointment, a plaster, a lotion, a liniment, a paste or a cataplasm, may be provided.

The pharmaceutical composition of the present disclosure may be administered orally or parenterally. Specifically, the parenteral administration is topical application.

A preferred administration dosage of the pharmaceutical composition of the present disclosure may be adequately determined by those skilled in the art, although it varies depending on the condition and body weight of a patient, the severity of a disease, drug type, administration route and administration period. In order to achieve the desired effect, the pharmaceutical composition of the present disclosure may be administered at a daily dosage of 0.0001-100 mg/kg, specifically 0.001-10 mg/kg. The administration may be made once or several times a day. The administration dosage does not limit the scope of the present disclosure in any way.

The pharmaceutical composition of the present disclosure may be prepared into any formulation that can be applied to the scalp, such as a liquid, a cream, a paste, a solid, etc. In addition, it may be prepared into a shampoo, a hair conditioner, a hair lotion, a liquid hair tonic, etc. for promoting hair growth by adding a common additive, and may also be prepared into an aerosol-type formulation thereof.

Accordingly, the pharmaceutical composition according to an aspect of the present disclosure may contain a pharmaceutically acceptable carrier or additive.

The pharmaceutical composition may be administered to various mammals including rat, mouse, livestock, human, etc., and may be administered, for example, by oral, intrarectal, intravenous, intramuscular, subcutaneous, intradural or intracerebroventricular administration. Accordingly, the pharmaceutical composition may be prepared into a common pharmaceutical formulation known in the art. The pharmaceutical composition may be prepared into any formulation including a preparation for oral administration, an injection, a suppository, a preparation for transdermal administration and a preparation for nasal administration without limitation. Specifically, it may be prepared into a formulation for oral administration such as a liquid, a suspension, a powder, a granule, a tablet, a capsule, a pill, an emulsion, a syrup, an aerosol or an extract.

Each formulation may be prepared by adding a pharmaceutically acceptable carrier or additive. As a representative example, a formulation for oral administration may be prepared using one or more selected from a diluent, a glidant, a binder, a disintegrant, a sweetener, a stabilizer and an antiseptic as a carrier, and one or more selected from a flavor, a vitamin and an antioxidant may be used as an additive.

The carrier or additive may be any pharmaceutically acceptable one. Specifically, the diluent may be lactose, dextrose, sucrose, corn starch, soybean oil, microcrystalline cellulose, sorbitol, xylitol or mannitol, the glidant may be magnesium stearate or talc, and the binder may be polyvinylpyrrolidone or hydroxypropyl cellulose. And, the disintegrant may be calcium carboxymethyl cellulose, sodium starch glycolate, polacrilin potassium or crospovidone, the sweetener may be white sugar, fructose, sorbitol or aspartame, the stabilizer may be sodium carboxymethyl cellulose, β-cyclodextrin, white beeswax or xanthan gum, and the antiseptic may be methyl p-oxybenzoate, propyl p-oxybenzoate or potassium sorbate.

In addition to the above-described ingredients, a natural flavor such as plum flavor, lemon flavor, pineapple flavor, herb flavor, etc., natural fruit juice, a natural coloring agent such as chlorophyllin, flavonoids, etc., a sweetening agent such as fructose, honey, sugar alcohol or sugar, or a sour taste agent such as citric acid or sodium citrate may be used as a known additive to improve taste.

Among the above-described preparations, preparations for parenteral administration include a sterilized aqueous solution, a nonaqueous solution, a suspension, an emulsion, a lyophilized preparation, a suppository, etc. For preparation of the nonaqueous solution or suspension, propylene glycol, polyethylene glycol, vegetable oil such as olive oil, an injectable ester such as ethyl oleate, etc. may be used. As a base of the suppository, witepsol, macrogol, Tween 61, cocoa butter, laurin butter, glycerogelatin, etc. may be used.

In order to achieve an effect of preventing or treating hair loss or prostatic hyperplasia, the pharmaceutical composition may be administered at a dosage of 0.01-10 g/kg/day, specifically 1-5 g/kg/day, based on the dry powder of the extract of the active ingredient of the composition, once to several times a day, and the administration dosage may be adequately increased or decreased depending on the age, sex, body weight and diet of a patient, excretion rate and co-administered medications. Accordingly, the pharmaceutical composition according to the present disclosure is prepared in consideration of the range of the effective amount, and the formulated unit dosage preparation may be administered using a specialized method or with predetermined time intervals depending on the discretion of an expert or the requirement for individuals.

The composition of the present disclosure may be a functional health food composition and may contain a sitologically acceptable carrier or additive.

In the present disclosure, the "functional health food" refers to a food which is prepared and processed from raw materials or ingredients having functionality useful for the human body as defined by the law regarding functional health food. The "functionality" means that the food is taken for the purpose of controlling nutrients with respect to the structure and function of the human body or obtaining useful effects for health such as physiological functions.

The functional health food composition according to the present disclosure may be formulated into a common functional health food known in the art. The functional health food may be prepared, for example, into a powder, a granule, a tablet, a pill, a capsule, a suspension, an emulsion, a syrup, an infusion, a liquid, an extract, a gum, a tea, a jelly, a beverage, etc. As the sitologically acceptable carrier or additive, any carrier or additive known in the art may be used.

The functional health food composition may contain a mixture of cucumber, eggplant and snail extracts, which is the active ingredient of the composition according to the present disclosure, in an amount of 0.01-20 wt %, specifically 0.2-10 wt %, based on the total food weight. When it is prepared as a beverage, it may contain the active ingredient in an amount of 0.1-30 g, specifically 0.2-5 g, per 100 mL.

The beverage may further contain other ingredients in addition to the extracts, and may further contain various flavorants, natural carbohydrates, etc. commonly used in beverages. The natural carbohydrates may include common sugars such as monosaccharides (e.g., glucose, fructose, etc.), disaccharides (e.g., maltose, sucrose, etc.) and polysaccharides (e.g., dextrin, cyclodextrin, etc.), and sugar alcohols such as xylitol, sorbitol, erythritol, etc. And, the flavorants may include natural flavorants (e.g., thaumatin, stevia extract, etc.) and synthetic flavorants (e.g., saccharin, aspartame, etc.). Specifically, the natural carbohydrate may be contained in an amount of generally about 1-20 g, specifically about 5-12 g, per 100 mL of the beverage.

Hereinafter, the present disclosure is described in more detail through specific examples, etc. However, these examples, etc. are for describing the present disclosure more specifically and it will be obvious to those having ordinary knowledge in the art that the scope of the present disclosure is not limited by them.

EXAMPLE 1-1

Preparation of Mixture of Cucumber, Eggplant and Snail Extracts

After mixing dried cucumber obtained by washing fresh cucumber, removing the top and bottom ends of about 2 cm, cutting vertically in half, removing cucumber seeds and then drying the same, dried eggplant obtained by removing the stalk of eggplant and then drying the same, and dried snail obtained by steaming snail for 10 minutes, removing the internal organs and then drying the same at a weight ratio of 4:2:1 and adding 10 weight equivalents of water, extraction was conducted at 90° C. for 10 hours and the extract was filtered under reduced pressure. The filtrate was concentrated using a vacuum evaporator and then freeze-dried to prepare an extract of cucumber, eggplant and snail.

EXAMPLE 1-2

Preparation of Mixture of Cucumber, Eggplant and Snail Extracts

Fresh cucumber was washed and the top and bottom ends of about 2 cm were removed. The fresh cucumber was cut vertically in half and cucumber seeds were removed. After adding 5 weight equivalents of water, extraction was conducted at 90° C. for 10 hours and the extract was filtered under reduced pressure. The filtrate was concentrated using a vacuum evaporator and then freeze-dried to prepare a cucumber extract.

Dried eggplant obtained by removing the stalk of eggplant and then drying the same was extracted at 90° C. for 10 hours after adding 5 weight equivalents of water. After filtration under reduced pressure, the filtrate was concentrated using a vacuum evaporator and then freeze-dried to prepare an eggplant extract.

After steaming snail for 10 minutes and removing the internal organs, extraction was conducted at 90° C. for 10 hours after adding 10 weight equivalents of water. After filtration under reduced pressure, the filtrate was concentrated using a vacuum evaporator and then freeze-dried to prepare a snail extract.

A mixture of cucumber, eggplant and snail extracts was prepared by mixing the cucumber extract, the eggplant extract and the snail extract at a weight ratio of 4:2:1.

EXAMPLE 1-3

Preparation of Mixture of Cucumber, Eggplant and Snail Extracts

A mixture of cucumber, eggplant and snail extracts was prepared by mixing the cucumber extract, the eggplant extract and the snail extract of Example 1-2 at a weight ratio of 2:2:1.

EXAMPLE 1-4

Preparation of Mixture of Cucumber, Eggplant and Snail Extracts

A mixture of cucumber, eggplant and snail extracts was prepared by mixing the cucumber extract, the eggplant extract and the snail extract of Example 1-2 at a weight ratio of 1:1:1.

COMPARATIVE EXAMPLE 1-1

Preparation of Mixture of Cucumber and Eggplant Extracts

A mixture of cucumber and eggplant extracts was prepared by mixing the cucumber extract and the eggplant extract of Example 1-2 at a weight ratio of 2:1.

COMPARATIVE EXAMPLE 1-2

Preparation of Mixture of Cucumber and Snail Extracts

A mixture of cucumber and snail extracts was prepared by mixing the cucumber extract and the snail extract of Example 1-2 at a weight ratio of 4:1.

COMPARATIVE EXAMPLE 1-3

Preparation of Mixture of Eggplant and Snail Extracts

A mixture of eggplant and snail extracts was prepared by mixing the eggplant extract and the snail extract of Example 1-2 at a weight ratio of 2:1.

EXAMPLE 2-1

Preparation of Mixture of Cucumber, Eggplant, Snail, Thuja Leaf and Sophora Root Extracts After mixing dried cucumber obtained by washing fresh cucumber, removing the top and bottom ends of about 2 cm, cutting vertically in half, removing cucumber seeds and then drying the same, dried eggplant obtained by removing the stalk of eggplant and then drying the same, and dried snail obtained by steaming snail for 10 minutes, removing the internal organs and then drying the same, dried thuja leaf and dried sophora root at a weight ratio of 4:2:1:1:1 and adding 10 weight equivalents of water, extraction was conducted at 90° C. for 10 hours and the extract was filtered under reduced pressure. The filtrate was concentrated using a vacuum evaporator and then freeze-dried to prepare a mixture of cucumber, eggplant, snail, thuja leaf and sophora root extracts.

EXAMPLE 2-2

Preparation of Mixture of Cucumber, Eggplant, Snail, Thuja Leaf, Sophora Root, Dried Ginger Rhizome, Eclipta, *Cynanchum wilfordii,* Chinese Angelica Root and Dihuang Extracts After mixing dried cucumber obtained by washing fresh cucumber, removing the top and bottom ends of about 2 cm, cutting vertically in half, removing cucumber seeds and then drying the same, dried eggplant obtained by removing the stalk of eggplant and then drying the same, and dried snail obtained by steaming snail for 10 minutes, removing the internal organs and then drying the same, dried thuja leaf, dried sophora root, dried ginger rhizome, dried eclipta, dried *Cynanchum wilfordii*, dried Chinese angelica root and dried dihuang at a weight ratio of 4:2:1:1:1:0.5:0.5:0.5:0.5:0.5 and adding 10 weight equivalents of water, extraction was conducted at 90° C. for 10 hours and the extract was filtered under reduced pressure. The filtrate was concentrated using a vacuum evaporator and then freeze-dried to prepare a mixture of cucumber, eggplant, snail, thuja leaf, sophora root, dried ginger rhizome, eclipta, *Cynanchum wilfordii*, Chinese angelica root and dihuang extracts.

EXAMPLE 2-3

Preparation of Mixture of Cucumber, Eggplant, Snail, Thuja Leaf, Sophora Root, Dried Ginger Rhizome, Eclipta, *Cynanchum wilfordii*, Chinese Angelica Root and Houttuynia Extracts After mixing dried cucumber obtained by washing fresh cucumber, removing the top and bottom ends of about 2 cm, cutting vertically in half, removing cucumber seeds and then drying the same, dried eggplant obtained by removing the stalk of eggplant and then drying the same, and dried snail obtained by steaming snail for 10 minutes, removing the internal organs and then drying the same, dried thuja leaf, dried sophora root, dried ginger rhizome, dried eclipta, dried *Cynanchum wilfordii*, dried Chinese angelica root and dried houttuynia at a weight ratio of 4:2:1:1:1:0.5:0.5:0.5:0.5:0.5 and adding 10 weight equivalents of water, extraction was conducted at 90° C. for 10 hours and the extract was filtered under reduced pressure. The filtrate was concentrated using a vacuum evaporator and then freeze-dried to prepare a mixture of cucumber, eggplant, snail, thuja leaf, sophora root, dried ginger rhizome, eclipta, *Cynanchum wilfordii*, Chinese angelica root and houttuynia extracts.

TEST EXAMPLE 1

Cytotoxicity in Human Fibroblasts

Since hair growth is regulated by the differentiation and proliferation of keratinocytes, melanocytes and fibroblasts (Hirobe T, *Histol Histopathol* 1995; 10: 223-237) and minoxidil facilitates the proliferation of various skin cells and hair follicle cells (Messenger A G, Rundegren J. *Br J Dermatol* 2004; 150: 186-194), the proliferation of fibroblasts is considered to be an important factor in hair growth.

Human fibroblasts (ATCC, American Type Culture Collection, Cat. No. CRL-2076) were seeded onto a 24-well plate at a concentration of $5 \times 10^4$ cells/mL. IMDM (Iscove's modified Dulbecco's medium; GIBCO, USA) containing 10% bovine serum was used as a medium. 24 hours later, after replacing the medium with IMDM (Iscove's modified Dulbecco's medium; GIBCO, USA) containing 0% bovine serum and adding 10 μL of a test sample (Example 1-1, 2-1, 2-2 or 2-3) at a concentration of 1, 10, 50 or 250 μg/mL, the cells were cultured in a 5% $CO_2$ incubator at 37° C. for 3 days. After the culturing was completed, the supernatant was removed. After washing by adding 200 μL of 5% PBS (phosphate-buffered saline) and then adding 1.0 mL of a 25 μg/mL MTT solution to each well, MTT was removed 4 hours later and absorbance was measured at 570 nm after adding 1.0 mL of DMSO to each well. Cell survival rate was calculated by dividing the absorbance of the sample at 570 nm by the absorbance of the negative control group at 570 nm and then multiplying 100. The result is shown in Table 1.

TABLE 1

| Sample concentration (μg/mL) | 1 | 10 | 50 | 250 |
|---|---|---|---|---|
| Negative control | 100% | 100% | 100% | 100% |
| Example 1-1 | 101.5% | 97.7% | 87.3%** | 85.1%** |
| Example 2-1 | 90.4%* | 96.4% | 90.5%* | 90.1%* |
| Example 2-2 | 95.8% | 96.7% | 97.1% | 96.6% |
| Example 2-3 | 98.7% | 100.1% | 98.7% | 105.2%** |

As a result of investigating the proliferation of the human fibroblasts, Examples 1-1 and 2-1 did not show cytotoxicity up to 10 μg/mL and showed a cell survival rate of 85% or higher even at 250 μg/mL. In particular, Example 2-2 did not show cytotoxicity up to 250 μg/mL, and Example 2-3 even increased cell survival rate at 250 μg/mL (**, $p<0.01$).

TEST EXAMPLE 2

Cytotoxicity in Dermal Papilla Cells

Dermal papilla cells are one of the major components of the hair dermal papilla, and growth factors produced and secreted by the dermal papilla cells (basic fibroblast growth factor (bFGF), endothelin-1 (ET-1), stem cell factor (SCF), etc.) facilitate the growth and differentiation of hair matrix cells (Paus R, Foitzik K. *Differentiation* 2004; 72: 489-511; Fujie T, et al., *J Dermatol Sci* 2001; 25: 206-212; Botchkarev V A, et al., *J Investig Dermatol Symp Proc* 2003; 8: 46-55). In general, they are considered to play a critical role in the induction of new hair follicles and the maintenance of hair growth (Jahoda C A, et al., *Nature* 1984; 311: 560-562; Kamp H, et al., *Exp Dermatol* 2003; 12: 662-672; Krugluger W, et al., *Exp Dermatol* 2005; 14: 580-585.). Accordingly, it can be said that the activation and proliferation of dermal papilla cells are important factors in the development of a new substance that promotes hair growth.

Dermal papilla cells were seeded onto a 24-well plate at a concentration of $5 \times 10^4$ cells/mL. DMEM (Dulbecco's modified Eagle's medium, BRL, USA) containing 10% bovine serum was used as a medium. 24 hours later, after replacing the medium with DMEM (Dulbecco's modified Eagle's medium, BRL, USA) containing 0% bovine serum and adding 10 μL of each of test samples (Examples 1-1, 2-1, 2-2 and 2-3) at a concentration of 1, 10, 50 or 250 μg/mL, the cells were cultured for 3 days at 37° C. in a 5% $CO_2$ incubator. After the culturing was completed, the supernatant was removed. After washing by adding 200 μL of 5% PBS (phosphate-buffered saline) and then adding 1.0 mL of a 25 μg/mL MTT solution to each well, MTT was removed 4 hours later and absorbance was measured at 570 nm after adding 1.0 mL of DMSO to each well. Cell survival rate was calculated in the same manner as in Test Example 1. The result is shown in Table 2.

TABLE 2

| Sample concentration (μg/mL) | 1 | 10 | 50 | 250 |
|---|---|---|---|---|
| Negative control | 100% | 100% | 100% | 100% |
| Example 1-1 | 105.1% | 111.5%* | 105.6% | 114.0%** |

TABLE 2-continued

| Sample concentration (μg/mL) | 1 | 10 | 50 | 250 |
|---|---|---|---|---|
| Example 2-1 | 105.4% | 112.5%* | 111.8%* | 116.5%** |
| Example 2-2 | 112.8%* | 115.5%* | 127.5%** | 123.6%** |
| Example 2-3 | 107.3%* | 111.9%* | 111.4%* | 117.9%** |

As a result of investigating the proliferation of the dermal papilla cells, the proliferation of the cells was increased significantly at concentrations of 10 μg/mL or higher for all the test groups (*, $p<0.05$; **, $p<0.01$).

TEST EXAMPLE 3

Investigation of Increase in Expression of Hair-Related Genes

RT-PCR (reverse transcription polymerase chain reaction) was conducted in order to investigate the effect on the expression of hair-related genes, insulin-like growth factor 1 (IGF-1), hepatocyte growth factor (HGF) and keratinocyte growth factor (KGF). Dermal papilla cells were seeded onto a 100-mm cell culture dish at a density of 80% and then cultured for 24 hours at 37° C. in a 5% $CO_2$ incubator. DMEM (Dulbecco's modified Eagle's medium, BRL, USA) containing 10% bovine serum was used as a medium. After adding 100 μg/mL of a sample (Examples 1-1, 1-2, 1-3 and 1-4; Comparative Examples 1-1, 1-2 and 1-3; Examples 2-1, 2-2 and 2-3) or 1 μg/mL minoxidil as a positive control group, the cells were cultured for 18 hours and RNA was isolated by adding 1 mL of Trizol (Invitrogen, USA) according to the Promega's method. After quantifying RNA at 260 nm using a UV detector, RT-PCR was conducted. The RT-PCR was conducted using a RT-PCR kit (All-in-one RT-PCR kit, SuperBio, Korea) under the condition of 40 cycles of reverse transcription at 50° C. for 30 minutes followed by inactivation of reverse transcriptase at 96° C. for 3 minutes, 94° C. for 30 seconds, 58° C. for 30 seconds and 72° C. for 1 minute. The result was represented as percentage (%) of expression relative to the negative control group (Table 3).

TABLE 3

|  | HGF | IGF-1 | KGF |
|---|---|---|---|
| Negative control | 100% | 100% | 100% |
| Positive control | 134.6%** | 119.0%** | 120.2%** |
| Example 1-1 | 143.9%** | 702.3%*** | 256.2%** |
| Example 1-2 | 152.8%*** | 625.9%*** | 242.4%*** |
| Example 1-3 | 126.0%** | 196.0%*** | 159.4%** |
| Example 1-4 | 93.9% | 116.7%* | 106.1%* |
| Comparative Example 1-1 | 110.9%* | 53.9%*** | 68.3%** |

TABLE 3-continued

|  | HGF | IGF-1 | KGF |
|---|---|---|---|
| Comparative Example 1-2 | 133.7%** | 46.5%*** | 91.9% |
| Comparative Example 1-3 | 106.6% | 5.9%*** | 68.2%** |
| Example 2-1 | 124.3%** | 214.9%** | 106.4%* |
| Example 2-2 | 131.6%** | 192.5%** | 132.1%** |
| Example 2-3 | 132.5%** | 138.1%** | 124.4%** |

The positive control group, minoxidil, significantly increased the expression level of HMF, IGF-1 and KGF as compared to the negative control group (**, $p<0.01$).

The effect of the mixture of cucumber, eggplant and snail extracts of Example 1-1 was comparable to that of the mixture of the cucumber extract, the eggplant extract and the snail extract of Example 1-2, and both significantly increased the expression level of HMF, IGF-1 and KGF as compared to the negative control group (, $p<0.01$; *, $p<0.005$). Examples 1-3 and 1-4 showed decreased expression level of HMF, IGF-1 and KGF with relatively lower weight ratio of the cucumber extract.

The mixture of cucumber and eggplant extracts without the snail extract of Comparative Example 1-1, the mixture of cucumber and snail extracts without the eggplant extract of Comparative Example 1-2, and the mixture of eggplant and snail extracts without the cucumber extract of Comparative Example 1-3 remarkably decreased the expression level of IGF-1 as compared to the negative control group (*, $p<0.005$), and Comparative Examples 1-1 and 1-3 significantly decreased the expression level of KGF (, $p<0.01$).

Examples 2-1, 2-2 and 2-3 significantly increased the expression level of HMF, IGF-1 and KGF (*, $p<0.05$; **, $p<0.01$).

TEST EXAMPLE 4

Animal Experiment for Investigating Hair Growth-Promoting Effect

Figure 1:
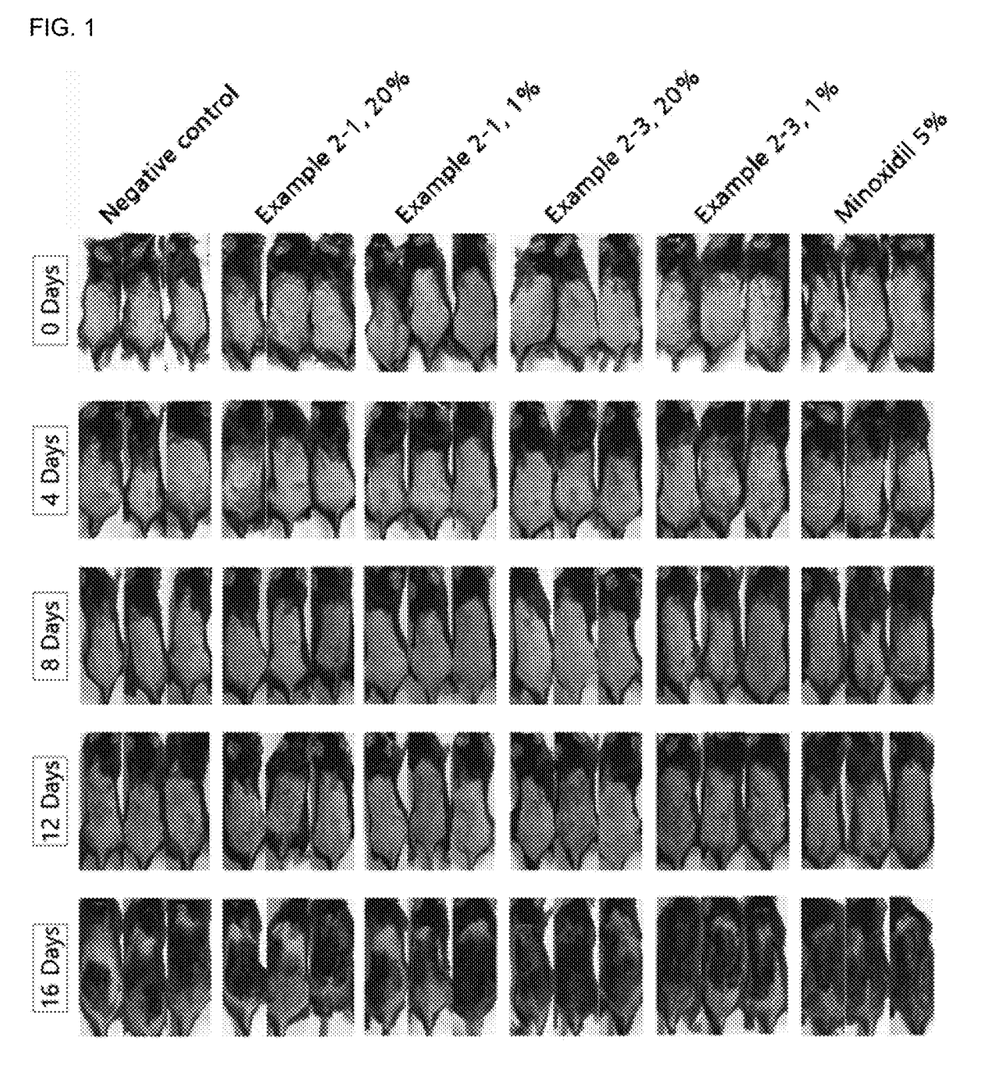
FIG. 1 shows the images of the back of mice of test groups tested in Test Example 4 for investigating hair-growing effect with time.

The hair growth-promoting effect of the composition of the present disclosure was investigated using C57BL/6 mice. 49- to 51-day-old C57BL/6N mice, in the second catagen, were depilated completely on the back using wax. While applying 0.2 mL of Example 2-1 or 2-3 at a solid content of 1 wt % or 20 wt %, or 5 wt % minoxidil as a positive control group, diluted in water, once a day for 16 days, hair-growing effect was monitored. Distilled water was used as a negative control group. The hair growth index with time was evaluated by the 3-point scale (see Table 4). FIG. 1 shows the images of the back of the mice during the test period. A score of 0 denoted no hair growth with pink skin color, 0.5 point indicated that the skin color was gray without visible hair growth, 1 point indicated that the skin color was gray or black without hair in the growing phase, 1.5 points indicated the appearance of some hair growth, 2 points indicated that short hairs were widespread, 2.5 points indicated that the hair were grown to medium length, and 3 points denoted that hair was completely grown densely.

TABLE 4

|  | Negative control | Example 2-1 (20%) | Example 2-1 (1%) | Example 2-3 (20%) | Example 2-3 (1%) | Minoxidil (5%) |
|---|---|---|---|---|---|---|
| Day 0 | 0 | 0 | 0 | 0 | 0 | 0 |
| Day 12 | 1.03 ± 0.42 | 1.13 ± 0.62 | 1.26 ± 0.16 | 1.45 ± 0.32 | 1.36 ± 0.16 | 1.22 ± 0.26 |
| Day 16 | 1.93 ± 0.62 | 2.13 ± 0.30 | 2..33 ± 0.24* | 2.76 ± 0.10* | 2.56 ± 0.47* | 2.66 ± 0.23* |

There was no visibly distinct difference between the test groups until day 12. On day 16, hair growth was observed in all the mice of the 20% administration group and 1% administration group of Example 2-1. Two out of four mice showed relative uniform hair growth on the back, while the others showed large difference in hair length. The 20% administration group and 1% administration group of Example 2-3 showed uniform hair growth as compared to the administration groups of Example 2-1 and had a longer hair length. In the 1% administration group of Example 2-3, one out of four mice showed fully grown hair on the back. The other three mice showed thickly grown hairs on the back, but the hairs above and below the back showed short hairs. The positive control group, i.e., the minoxidil 5% administration group, showed hair growth on the back, but the hair length was relatively short as compared to other groups.

TEST EXAMPLE 5

Clinical Test

Forty male and forty female subjects (55-78 years, residing in Yeoju, Gyeonggi-do, Korea) with the symptoms of hair loss were randomly divided into 4 groups of 20 people, and were asked to use the shampoo described in Table 5 for 3 months, once a day before going to bed.

TABLE 5

|  | Negative control | Example 2-1 | Example 2-3 |
| --- | --- | --- | --- |
| Extract of Example | 0 | 50 | 50 |
| LES | 462 | 462 | 462 |
| Cocobetaine | 216 | 216 | 216 |
| Apple Wassail | 246 | 246 | 246 |
| Polyquaternium | 13 | 13 | 13 |
| Glutamate | 47 | 47 | 47 |
| Glycerin | 46 | 46 | 46 |
| Panthenol | 46 | 46 | 46 |
| Silk amino acid | 46 | 46 | 46 |
| Marine elastin | 46 | 46 | 46 |
| Phenoxyethanol | 0.5 | 0.5 | 0.5 |
| 1,2-Hexanediol | 2 | 2 | 2 |
| Purified water | 750 | 750 | 750 |

The condition of the hair and scalp of the subjects who used each shampoo were observed 3 months later. The improvement of the hair loss and the improvement of the condition of the hair and scalp were evaluated by the 5-point scale (1 point: worsened, 2 points: no change, 3 points: slightly improved, 4 points: improved, 5 points: improved greatly). The average score is given in Table 6.

TABLE 6

|  | Negative control | Example 2-1 | Example 2-3 |
| --- | --- | --- | --- |
| Hair growth | 2.2 | 4.8 | 4.6 |
| Improvement of dandruff | 2.0 | 4.8 | 4.6 |
| Improvement of scalp inflammation | 2.0 | 4.4 | 4.6 |
| Improvement of scalp itching | 1.4 | 4.0 | 4.2 |
| Decrease in hair loss | 2.0 | 4.7 | 4.6 |
| Overall satisfaction | 2.2 | 4.8 | 4.7 |

Examples 2-1 and 2-3 showed excellent effect in growth of new hair and alleviation or improvement of scalp inflammation, and showed superior effect also in the improvement of hair thickness and rigidity. Accordingly, most of the subjects who participated in the test expressed satisfaction.

Figure 2:
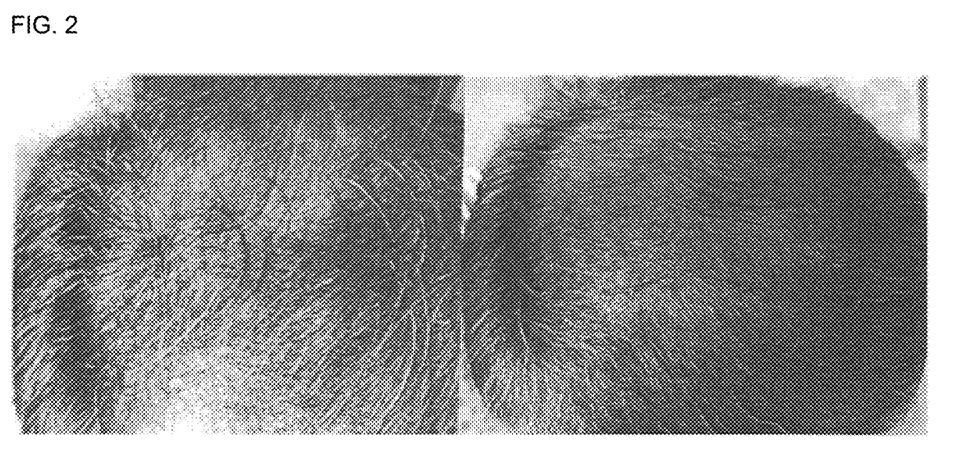
FIG. 2 shows the images showing hair growth around the crown of the head of a participant before and after testing in Test Example 5.

FIG. 2 shows the images showing the change in hair around the crown of the head of a subject who participated in the test before and after the test (left: before test, right: after use for 3 months). It can be seen that hair density was increased around the crown of the head of the subject.

We claim:

1. A method for promoting hair growth, comprising administering a cosmetic or pharmaceutical composition comprising a mixture of a cucumber extract, an eggplant extract, and a snail (Gastropoda) extract, as active ingredients to a subject in need thereof,
wherein the cucumber extract, the eggplant extract, and the snail (Gastropoda) extract are each a dry powder from an aqueous extraction,
wherein the content of the cucumber extract is 8-16 parts by weight, the content of the eggplant extract is 4-8 parts by weight, and the content of the snail (Gastropoda) extract is 1-4 parts by weight,
wherein the cucumber extract is obtained from a fruit wherein about 1-3 cm of a bitter-tasting top end and a bitter-tasting bottom end had been removed,
wherein the eggplant extract is obtained from a fruit wherein the stalk had been removed, and
wherein the snail (Gastropoda) extract is obtained from steaming the snail (Gastropoda) from which internal organs had been removed.

2. The method according to claim 1, wherein the cosmetic or pharmaceutical composition further comprises a mixture of *Thuja orientalis L.* leaves and *Sophora flavescens* root extracts.

3. The method according to claim 2, wherein the cosmetic or pharmaceutical composition further comprises an extract of one or more selected from the group of dried *Rehmanniae radix*, dried ginger rhizome, *Angelica sinensis* root, *Eclipta, Cynanchum wilfordii*, foxtail millet and brown rice.

4. The method according to claim 3, wherein the cosmetic or pharmaceutical composition further comprises an extract of one or more selected from the group of *Houttuynia* and licorice.

5. The method according to claim 2, wherein the cosmetic composition is one selected from the group of a hair tonic, a hair conditioner, a hair essence, a hair lotion, a hair-nourishing lotion, a hair shampoo, a hair rinse, a hair treatment, a hair cream, a hair-nourishing cream, a hair-moisturizing cream, a hair massage cream, a hair wax, a hair aerosol, a hair pack, a hair-nourishing pack, a hair soap, a hair-cleansing foam, a hair oil, a hair-drying preparation, a hair-preserving preparation, a hair dye, a hair-waving preparation, a hair bleach, a hair gel, a hair glaze, a hairdressing preparation, a hair lacquer, a hair moisturizer, a hair mousse and a hair spray.

6. The method of claim 1, wherein a weight ratio of the cucumber extract to the eggplant extract to the snail (Gastropoda) extract is 4:2:1.

7. The method of claim 1, wherein a weight ratio of the cucumber extract to the eggplant extract to the snail (Gastropoda) extract is 2:2:1.

* * * * *